(12) United States Patent
Björling et al.

(10) Patent No.: US 7,181,279 B2
(45) Date of Patent: Feb. 20, 2007

(54) IMPLANTABLE HEART STIMULATING DEVICE, SYSTEM AND METHOD

(75) Inventors: Anders Björling, Järfälla (SE); Nils Holmström, Järfälla (SE); Karin Järverud, Solna (SE)

(73) Assignee: St. Jude Medical AB, Jarfalla (CH)

( * ) Notice: Subject to any disclaimer, the term of this patent is extended or adjusted under 35 U.S.C. 154(b) by 336 days.

(21) Appl. No.: 10/781,171

(22) Filed: Feb. 18, 2004

(65) Prior Publication Data
US 2004/0230234 A1 Nov. 18, 2004

(30) Foreign Application Priority Data
Feb. 18, 2003 (SE) .................................. 0300446

(51) Int. Cl.
*A61N 1/36* (2006.01)
(52) U.S. Cl. .......................................................... 607/9
(58) Field of Classification Search .................... 607/9, 607/14, 18, 27, 28
See application file for complete search history.

(56) References Cited

U.S. PATENT DOCUMENTS

| | | | |
|---|---|---|---|
| 5,643,326 A | 7/1997 | Weiner et al. | |
| 5,720,768 A | 2/1998 | Verboven-Nelissen | |
| 6,070,100 A | 5/2000 | Bakels et al. | |
| 6,128,535 A * | 10/2000 | Maarse | 607/28 |
| 6,466,820 B1 | 10/2002 | Juran et al. | |
| 2002/0183792 A1 | 12/2002 | Struble | |
| 2003/0023281 A1 | 1/2003 | Busch et al. | |
| 2003/0208238 A1 * | 11/2003 | Weinberg et al. | 607/9 |

FOREIGN PATENT DOCUMENTS

| | | |
|---|---|---|
| EP | 3 308535 | 3/1989 |
| EP | 0 451 498 | 10/1991 |
| EP | 1 199 085 | 4/2002 |

\* cited by examiner

*Primary Examiner*—Robert E. Pezzuto
*Assistant Examiner*—Eric D. Bertram
(74) *Attorney, Agent, or Firm*—Schiff Hardin LLP (57) ABSTRACT

An implantable bi-ventricular heart stimulating device and system operate, within a time cycle, to deliver pacing pulses with both a first and a second pacing circuit with a first time delay between these pacing pulses. The device employs a criterion with which a signal typical for a premature ventricular contraction is detected. The device also operates with a second time delay and/or with a third time delay, and, if a predefined pacing rule is fulfilled, to deliver a pacing pulse with the second time delay or said third time delay. The risk for arrhythmia in connection with a PVC is reduced.

42 Claims, 4 Drawing Sheets

FIG 4

IMPLANTABLE HEART STIMULATING DEVICE, SYSTEM AND METHOD

BACKGROUND OF THE INVENTION

1. Field of the Invention

The present invention relates to an implantable heart-stimulating device with which it is possible to stimulate both ventricles of a heart, i.e. a bi-ventricular pacer.

The invention also relates to a system including such a device and to the use of the system.

2. Description of the Prior Art

Several different implantable devices for stimulating a heart are known. The devices are normally able to sense the electrical activity of the heart. Some implantable devices are able to deliver stimulation pulses to both the left and right ventricles of the heart, and sometimes also to the left and right atria.

Devices that are able to deliver stimulation pulses to both the left and right ventricles are also called bi-ventricular pacers. Such de-vices can be used to treat patients who suffer from different severe cardiac problems, e.g. patients suffering from congestive heart failure (CHF). CHF is defined generally as the inability of the heart to deliver a sufficient amount of blood to the body. CHF can have different causes. It can be caused, for example, by a left bundle branch block (LBBB) or a right bundle branch block (RBBB). By for example using bi-ventricular pacing, the contraction of the ventricles can be controlled in order to improve the ability of the heart to pump blood. The stimulation pulses to the two ventricles can be delivered simultaneously but it is also known to deliver the stimulation pulses to the two ventricles with a short time delay (VV) between them in order to optimize the pumping performance of the heart.

U.S. Pat. No. 5,720,768 describes different possible electrode positions in order to stimulate or sense the different chambers of the heart.

U.S. Pat. No. 6,070,100 describes that electrodes may be positioned in both the left and the right atrium as well as in the left and the right ventricles.

Another phenomenon known in connection with heart stimulation devices (pacers) is premature ventricular contraction (PVC). PVC means, as the expression suggests, that the ventricle in question contracts too early. The occurrence of PVCs can lead to un-wanted consequences in pacers. For example, a PVC may be sensed by an electrode located in the atrium and thereby be interpreted by the pacer as an atrial event. This may cause so-called pacemaker mediated tachycardia (PMT). This problem has been solved in different manners in pacers having means for sensing and pacing the right atrium and the right ventricle. One known manner of treating this problem is that the pacer, when detecting a PVC, initiates an extended post-ventricular atrial refractory period (sometimes designated +PVARP), i.e. a period during which the atrial channel's sensing is unresponsive.

In bi-ventricular pacers, the situation is more complex, since this kind of pacer usually has more sensing and pacing electrodes, and therefore, more signals are detected or generated by the pacer. Techniques are known, however, for preventing PMT also in bi-ventricular pacers. The document U.S. Publication application 2002/0183792 A1 describes a pacer with an extended PVARP-function, in which a certain ventricular blanking period (designated 430 in the document) is used to prevent an unwanted dual PVC response, which could otherwise occur in a bi-ventricular pacer.

There also exist different manners of operating a bi-ventricular pacer. When an event is detected in one ventricle it is possible to immediately deliver a pacing pulse to the same ventricle or only to the other ventricle or to both ventricles. Sometimes the pacing pulse to the other ventricle is delivered with a time delay (VV), if that ventricle is the ventricle that should be paced later than the first ventricle. For example U.S. Pat. No. 6,466,820 discusses different pacing modes (see in particular column 15, lines 24–39). According to this document, in one manner of operating the device, also a PVC (if it arrives sufficiently late in the cardiac cycle) causes a pacing pulse to be delivered to the other ventricle with the normal programmed VV-delay. However, the document does not disclose any separate time interval for the treatment of PVCs.

Even if PMT caused by sensing a PVC in an atrium is prevented in accordance with the prior art, a PVC may still cause arrhythmic problems. For, for example, a patient suffering from a conduction block (for example a LBBB or a RBBB) PVCs can cause ventricular arrhythmia. Because of the block, the left and right ventricle do not depolarize synchronously as in a healthy heart. Since a PVC means that a depolarization takes place earlier than normally, a more complex situation with different degrees of depolarization in different parts of the heart takes place. This increases the likelihood of arrhythmic episodes.

SUMMARY OF THE INVENTION

An object of the present invention is to reduce the risk for arrhythmia in a bi-ventricular heart-stimulating device of this kind. A more particular object is to reduce the risk for arrhythmia that may be caused by PVCs in such a heart-stimulating device. A further object is to provide such a heart-stimulating device, in which, in addition to reducing the risk for such an arrhythmia, also the hemodynamic performance of the heart is favored in case of PVCs.

This object is achieved in accordance with the invention by an implantable heart stimulating device having a first pacing circuit connectable to a first pacing electrode suited to be positioned in or at a first ventricle of a heart such that the first pacing circuit delivers pacing pulses to the first pacing electrode in order to pace the first ventricle, a first sensing circuit connectable to a first sensing electrode suited to be positioned in or at said first ventricle of the heart so as to transfer signals to the first sensing circuit such that the first sensing circuit senses the first ventricle, a second pacing circuit connectable to a second pacing electrode suited to be positioned in or at a second ventricle of the heart such that the second circuit delivers pacing pulses to the second pacing electrode in order to pace the second ventricle, a second sensing circuit connectable to a second sensing electrode suited to be positioned in or at the second ventricle of the heart so as to transfer signals to the second sensing circuit such that the second sensing circuit senses the second ventricle, and a control circuit that operates with time cycles corresponding to normal heart cycles, the control circuit operating with a first time delay (VV) and, within one of the time cycles, pacing and/or sensing with the first pacing circuit or the first sensing circuit and then delivering a pacing pulse with the second pacing circuit with the first time delay, and the control circuit employing a criterion which, if satisfied by a signal that is sensed by the first or second sensing circuit, causes that signal to be categorized belonging to a first category of signals typical for a premature ventricular contraction. The control circuit also operates with a second time delay ($VV_{PVC1}$) and/or a third time delay ($VV_{PVC2}$), and, within one of the time cycles, senses with one of the first and second sensing circuits and then, at least if a predefined pacing rule is fulfilled, delivers a pacing pulse, with the second time delay ($VV_{PVC1}$) with the second pacing circuits if the sensing was done with the first sensing circuits or with the third time delay ($VV_{PVC2}$) with the first pacing circuits if the sensing was done with the second sensing circuit.

The device is thus arranged to operate with a first time delay VV as well as with at least one additional time delay, $VV_{PVC1}$ and/or $VV_{PVC2}$. The first time delay can be set to optimize the synchronization of the contraction of the ventricles. With the first time delay VV, the hemodynamic performance of the heart may thus be optimized. The second and/or third time delays can be set to a different value than VV. The second and/or third time delays may be set to reduce the risk for arrhythmia in certain situations. In particular, as has been described above, a PVC may cause a ventricular arrhythmia. In order to reduce the risk for such an arrhythmia, it is important to try to avoid a situation where the ventricles are in different states concerning depolarization. By setting an appropriate $VV_{PVC1}$ and/or $VV_{PVC2}$, the depolarization of the two ventricles can be optimized such that they occur synchronously. Thereby, the likelihood of arrhythmia is reduced. It should be pointed out that the best time delay for achieving simultaneous contraction of the ventricles may not be the same as the optimal time delay in order to synchronize the depolarization of the ventricles. Therefore, according to the present invention, since the second and/or third time delays $VV_{PVC1}$, $VV_{PVC2}$ can be set to be different from the first time delay VV, the operation of the device is optimized in order to reduce the risk for arrhythmia at the same time as the device, in its normal operation, is optimized for synchronizing the contraction of the ventricles.

Preferably, the device is programmable such that a physician can program the first and the second and/or third time delays. In a particular situation, it could be that a time delay is equal to zero, however, preferably both the first and at least one of the second and third time delays are not equal to zero.

It should also be pointed out that because of hardware reasons, even if a time delay is actually "set" to be zero, there may be a very small time between the delivered pulses to the two ventricles. When it is stated herein that a time delay is not equal to zero, it is thus meant that the time delay is purposely made longer than the minimum necessitated by the hardware.

It should be noted that the first ventricle can be either the left ventricle or the right ventricle. If the device is operated with a first time delay VV, then the ventricle to which a pacing pulse is delivered with the first time delay is designated the second ventricle. The first ventricle is thus the ventricle that is paced first if pacing pulses are delivered to both the ventricles.

It should also be noted that it is also possible for the device top operate with two different values of the first time delay VV. A first value of VV may be employed if the first ventricle is sensed and a second value of the time delay VV can be used if the first ventricle is paced. However, for simplicity it is below not further discussed that the first time delay in fact could have two different values.

Preferably, each of the first, second and third time delays is shorter than 80 ms, most preferably shorter than 40 ms. Such lengths of the mentioned time delays are normally beneficial in order to synchronize the contraction of the ventricles or to reduce the risk for arrhythmia in the event of a PVC.

The first time delay is preferably different from one or both of the second and third time delays. In particular, it is preferred that the first time delay is longer than the second and/or third time delay. In order to synchronize the depolarization of the two ventricles, the optimal time delay is normally shorter than the time delay for synchronizing the contraction of the ventricles.

In a preferred embodiment, the control circuit operates to determine whether a signal sensed by the first or second sensing circuit belongs to the aforementioned category, and, if this is the case, to deliver a pacing pulse, in accordance with the predefined pacing rule, with the first pacing circuit if the signal in the category was sensed by the second sensing circuit and with the second pacing circuit if the signal in the category was sensed by the first sensing circuit. When a signal typical of a PVC is detected by, for example, the first sensing circuit, a pacing pulse is delivered with the second pacing means. In this manner, the depolarization of the ventricles can be synchronized. At the same time also the hemodynamic performance is improved, since also the contraction of the ventricles, in case of a PVC, is likely to be more synchronized than if no such pacing pulse were delivered with the second pacing circuit.

Preferably, if the signal in the category is sensed by the first sensing circuit, then the pacing pulse delivered with the second pacing circuit is delivered with the second time delay ($VV_{PVC1}$). The second pacing circuit can be used to pace the second ventricle. The occurrence in time of the pacing pulse delivered with the second pacing circuit is optimized since it is delivered with the second time delay as has been described above. Analogously, if the signal in the category is sensed by the second sensing circuit, then the pacing pulse delivered by the first pacing circuit is delivered with the third time delay ($VV_{PVC2}$).

In an embodiment, after the signal in the category is sensed by the first sensing circuit, the control circuit monitors whether a corresponding signal is sensed by the second sensing circuit, and if such a signal is sensed by the second sensing circuit during said second time delay ($VV_{PVC1}$), then the delivery of the pacing pulse with the second pacing circuit is inhibited. If a signal is sensed by the second sensing circuit during the second time delay, then it is not necessary to deliver a pacing pulse with the second pacing circuit. Consequently, such a pacing pulse can be inhibited. Analogously, after a signal in the first category is sensed by the second sensing circuit, the control circuit can monitor whether a corresponding signal is sensed by the first sensing circuit, and if such a signal is sensed by the first sensing circuit during the third time delay ($VV_{PVC2}$), then the delivery of the pacing pulse with the first pacing circuit is inhibited.

In another embodiment, if a signal is sensed by the second sensing circuit, then the pacing pulse delivered by the first pacing circuit is delivered immediately (i.e. the third time delay $VV_{PVC2}$ is substantially equal to 0) upon sensing with the second sensing circuit. Since the pacing pulse normally should be delivered first with the first pacing circuit, it can be advantageous to deliver this pacing pulse as soon as possible in case the second sensing circuit senses a signal.

The device also can include an arrangement adapted to be able to sense and/or pace an atrium of the heart. It is well known to those skilled in the art that it is often advantageous to operate the device with sensing and/or pacing of one or both the atria of the heart, in addition to the ventricles.

In a preferred embodiment, the aforementioned criterion for categorizing a signal in the category is that either a signal is sensed by the first sensing circuit after a previous sensed or paced or inhibited event relating to the first sensing or pacing circuit without any intermediate sensed or paced event by the arrangement for sensing and pacing an atrium, or that a signal is sensed by the second sensing circuit after a previous sensed or paced or inhibited event relating to the second sensing or pacing circuit without any intermediate sensed or paced event by the arrangement for sensing and pacing an atrium. This is one practical way of categorizing a signal as a suspected PVC. Such a manner of detecting a PVC-signal is known in the art, however, the invention is not limited to this particular embodiment. It may also be possible to categorize a signal as a PVC by other criteria, such as the occurrence of a signal within a certain time window. Another possible criterion for categorizing a signal as a PVC is that the signal morphology satisfies certain predetermined morphology criteria, such as signal duration or sequence of peaks.

The above objects also are achieved in accordance with the invention, by an implantable heart stimulating system including a device according to any of the above embodiments and a first lead and a second lead connected to the device, wherein the first pacing electrode is arranged on the first lead and the second pacing electrode is arranged on the second lead. Preferably, the first sensing electrode is the same electrode as the first pacing electrode and the second sensing electrode is the same electrode as the second pacing electrode. With such a system, the advantages described above are achieved.

The invention is used by implanting the system in a human or animal, with the first pacing electrode positioned in or at a first ventricle of the heart of human or animal and the second pacing electrode being positioned in or at the second ventricle of the heart.

The heart stimulating system preferably is used to react to a premature ventricular contraction such that the risk for arrhythmia is reduced. The system can be used to treat a human or animal suffering from congestive heart failure, for example when the human or animal suffers from a bundle branch block.

DESCRIPTION OF THE PREFERRED EMBODIMENTS

Figure 1:
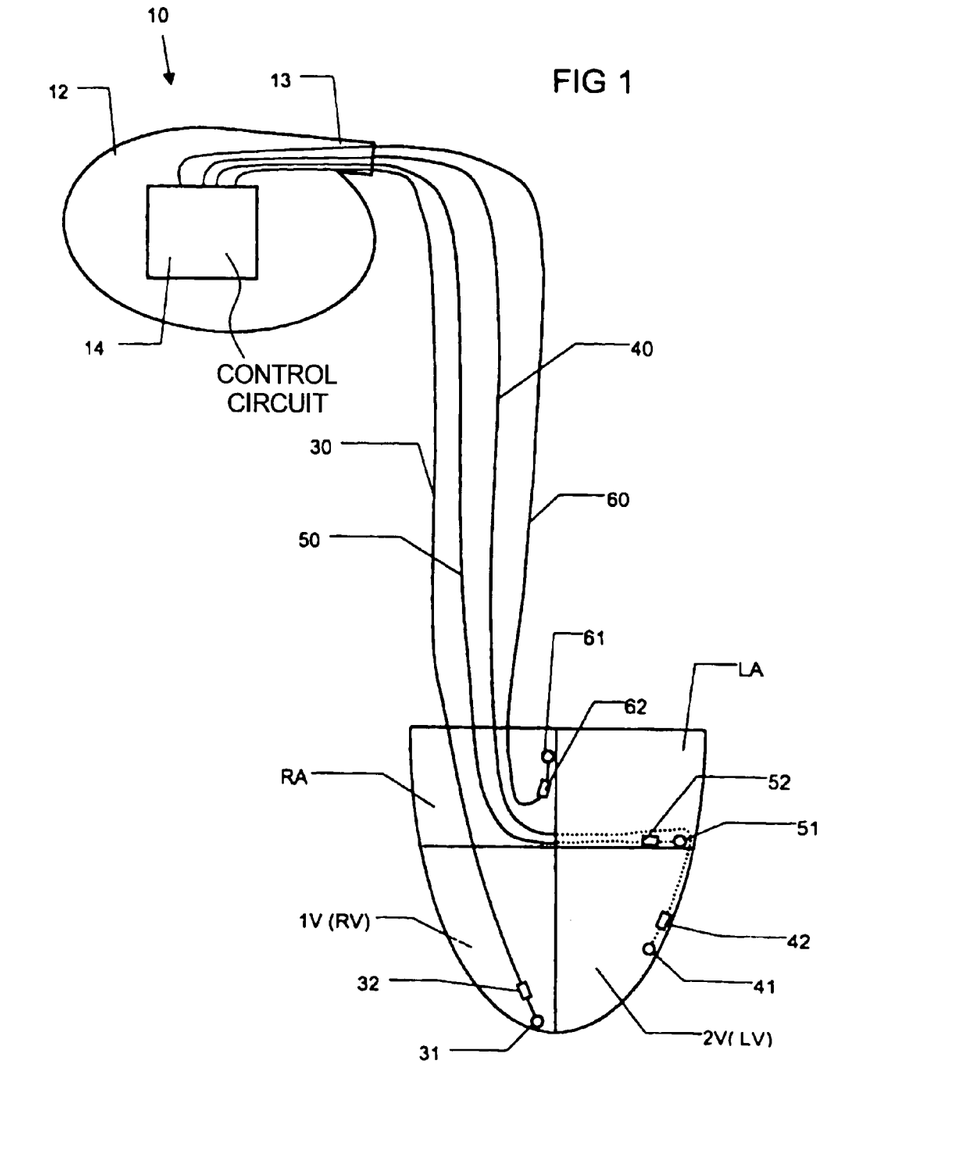
FIG. 1 schematically illustrates a heart stimulating system with a heart-stimulating device connected to leads with sensing and pacing electrodes positioned in a heart, in accordance with the invention.

FIG. 1 schematically shows an implantable heart-stimulating device 10 according to the invention. The device 10 has a housing 12. The device 10 contains a control circuit 14 (that will be described more in connection with FIG. 2). The device 10 has a connector portion 13. The device 10 is in the illustrated embodiment connected to different leads 30, 40, 50, 60.

FIG. 1 also schematically shows a heart having a right atrium RA, a left atrium LA, a right ventricle RV and a left ventricle LV.

A first lead 30 includes electrode members 31, 32 positioned in the right ventricle RV of the heart. The electrode member 31 may be called a tip electrode and the electrode member 32 can be called a ring electrode. In this example, the first lead 30 thus includes a bipolar electrode. However, it is within the scope of the invention that the device 10 instead is connected to unipolar electrodes as is known to those skilled in the art. The electrode formed by the electrode members 31, 32 constitutes a first sensing electrode suited to sense cardiac events related to a first ventricle 1V (in this case the right ventricle RV). The electrode formed by the electrode members 31, 32 also functions as a first pacing electrode for delivering pacing pulses to the first ventricle 1V.

A second lead 40 is connected to the device 10. The second lead 40 includes in the shown embodiment a bipolar electrode formed by electrode members 41, 42. These electrode members 41, 42 form a second sensing electrode positioned for sensing events related to the second ventricle 2V (in this case the left ventricle LV). The electrode members 41, 42 also form a second pacing electrode for delivering pacing pulses to the second ventricle 2V. The second lead 40, for example, may be introduced via the right atrium and the coronary sinus such that the electrode members 41, 42 are positioned in for example the middle or great cardiac vein of the heart. How to introduce the second lead 40 in this manner is known to those skilled in the art.

According to the shown embodiment, the device is also connected to a third lead 60 with a bipolar electrode formed by electrode members 61, 62. This electrode is positioned in the right atrium RA in order to be able to sense and pace this atrium. The device 10 in this case also is connected to a fourth lead 50 with a bipolar electrode formed by electrode members 51, 52. This electrode may be positioned in the coronary sinus in order to sense and pace the left atrium LA of the heart. According to an alternative embodiment the electrode formed by electrode members 41, 42 and the electrode formed by electrode members 51, 52 could be arranged on one and the same lead.

The device 10 together with at least two leads 30, 40 thus constitute an implantable heart stimulating system according to the invention.

Figure 2:
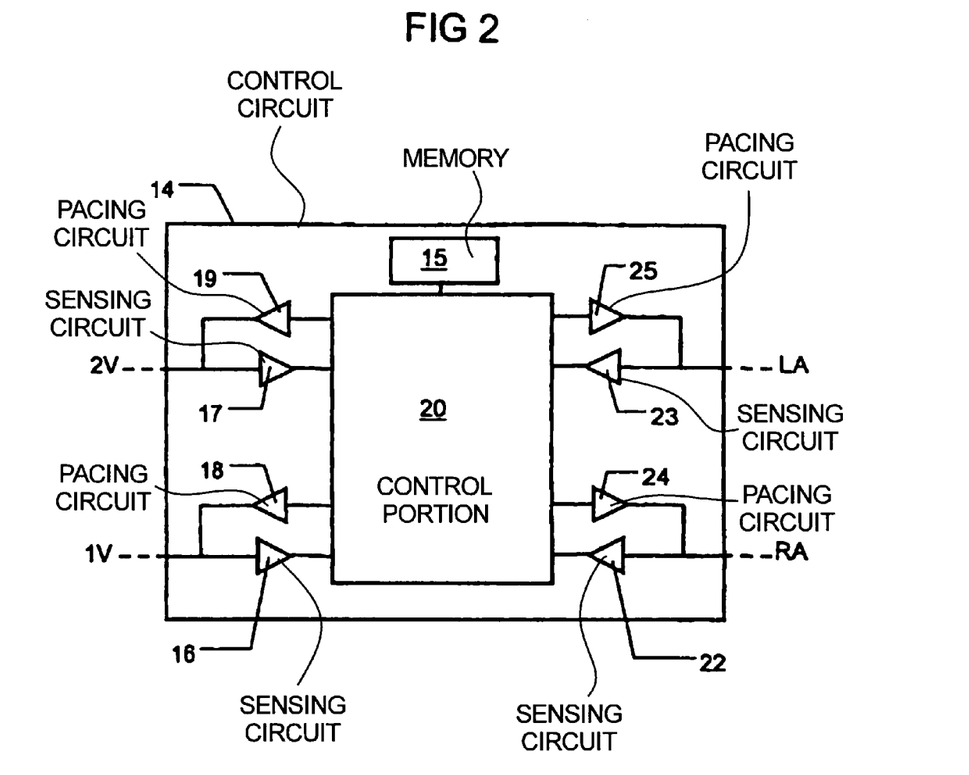
FIG. 2 schematically illustrates a control circuit that may form part of the device, in accordance with the invention.

FIG. 2 schematically shows the control circuit 14 in more detail. The control circuit 14 includes at least one memory 15. Furthermore, the control circuit 14 includes a first sensing circuit 16 and a first pacing circuit 18. These circuits 16 and 18 are adapted to be connected to the first lead 30 in order to sense and pace a first ventricle 1V. The circuits 16, 18 also are connected to a control portion 20 of the control circuit 14.

The control circuit 14 also includes a second sensing circuit 17 and a second pacing circuit 19. These circuits 17, 19 are adapted to be connected to the second lead 40 in order to sense and stimulate the second ventricle 2V. The circuits 17, 19 also are connected to the control portion 20 of the control circuit 14.

The control circuit 14 illustrated in FIG. 2 also includes a third sensing circuit 22 and third pacing circuit 24. These circuits 22, 24 are adapted to be connected to the third lead 60 in order to sense and pace the right atrium RA. The control circuit 14 also includes a fourth sensing circuit 23 and a fourth pacing circuit 25. These circuits 23, 25 are adapted to be connected to the fourth lead 50 in order to sense and pace the left atrium LA.

Since a control circuit 14 for controlling a pacer is well known to those skilled in the art, no further details need to be described herein. FIG. 2 functionally shows only some of the components of the control circuit 14 and the control circuit 14 does not necessarily have to be designed in the manner indicated in FIG. 2. The control circuit 14 may of course include several other components. For example the control circuit 14 can be arranged to control the heart-stimulating device 10 by sensing the level of physical activity of the living being into which the device 10 is implanted. Furthermore, the control circuit 14 can be arranged such that it can communicate via called telemetry with an external device. The control circuit 14 also for example may include means for delivering defibrillation signals. It also should be noted that the control circuit 14 may include several different memories, such as a RAM and a ROM.

The control circuit 14 operates with time cycles corresponding to normal heart cycles. This can be done by detecting signals typical for certain events in the heart and/or by preset timer intervals as is known to those skilled in the art.

The control circuit 14 detects R-waves (i. e. a QRS complex) in the two ventricles with the circuits 16, 17. The control circuit 14 detects such R-waves in a certain window, but preferably the control circuit 14 is arranged to continuously monitor the respective ventricles 1V, 2V for the detection of R-waves, except for during short blanking periods. Normally, the control circuit 14 also has a ventricular refractory period after the sensing of an R-wave (or after the delivery of a pacing pulse).

The control circuit 14 also can detect P-waves with the circuits 22 and/or 23.

The control circuit 14 also operates with a first time delay VV. Within the same time cycle, the device 10 may thus first pace and/or sense with the first pacing circuit 18 or the first sensing circuit 16 and then deliver a pacing pulse with the second pacing circuit 19 at the timeout of the first time delay VV. Such an operation is known in connection with bi-ventricular pacers. Thereby, the contraction of the ventricles can be synchronized.

The control circuit 14 also categorizes a signal as belonging to a category. The category of signals represents signals that are typical for a PVC. A signal can be categorized as a PVC-signal in different manners, for example by the fact that a sensed ventricular event is not preceded by a sensed or paced atrial event in the time cycle in question. This can be detected by the fact that a ventricular event is sensed after a previous sensed or paced or inhibited ventricular event in the same ventricle without an intermediate sensed or paced event relating to an atrium.

Another manner of detecting a PVC is by the fact that a sensed ventricular event is sensed after a previous sensed and/or paced ventricular event relating to any of the ventricles. According to this manner of detecting a PVC, the pacer preferably should be programmed with a refractory period of, for example, between 300 ms and 350 ms after a first sensed or paced event in a ventricle in order not to interpret a sensed event in the other ventricle within this refractory period as a PVC. Once such a PVC has been detected, the aforementioned refractory period can be disabled in order to allow for sensing during the below described second and third time delays $VV_{PVC1}$ and $VV_{PVC2}$.

Another possible criterion for categorizing a signal as a PVC is that the signal morphology fulfils certain predetermined morphology criteria, such as signal duration or sequence of peaks.

In addition to the aforementioned first time delay VV, the control circuit 14 operates with a second time delay $VV_{PVC1}$ and/or with a third time delay $VV_{PVC2}$. The Within the same time cycle, the control circuit 14 first senses with one of the first and second sensing circuits 16 and 17 and then, if a predefined pacing rule is fulfilled, deliver a pacing pulse, with the second time delay ($VV_{PVC1}$) with the second pacing circuit 19 if the sensing was done with the first sensing means 16 or with the third time delay ($VV_{PVC2}$) with the first pacing circuit 18 if the sensing was done with the second sensing circuit 17.

The first time delay VV, the second time delay $VV_{PVC1}$ and the third time delay $VV_{PVC2}$ preferably are programmable independently of each other. For example, the device may allow a physician to program these delays by telemetry. Each of the first time delay VV, the second time delay $VV_{PVC1}$ and the third time delay $VV_{PVC2}$ preferably is shorter than 80 ms, normally shorter than 40 ms. Preferably, the second time delay $VV_{PVC1}$ and the third time delay $VV_{PVC2}$ are set to be shorter than the first time delay VV.

Although not described in more detail, the device 10 of course may operate with features known to those skilled in the art. For example, the device 10 may detect evoked responses to delivered pacing pulses and to deliver back-up pulses when necessary. The device 10 also may inhibit pacing pulses when detecting intrinsic events. The device 10 may operate with particular timer intervals in order to avoid PMT. The device thus may include the +PVARP-function described above.

According to the invention, the device 10 preferably operates in the manner that will now be described in connection with FIGS. 3A, 3B and 4.

Figure 3A:
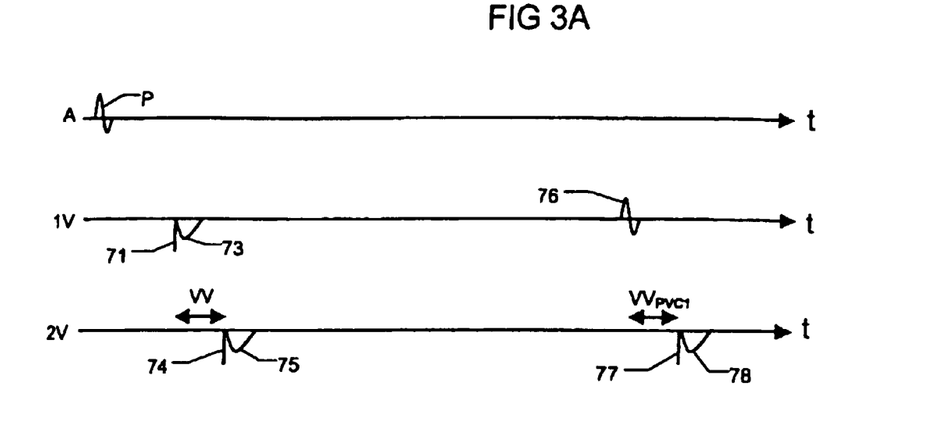
FIG. 3A schematically illustrates a signal sequence in a first situation of operation of the device, in accordance with the invention.

FIG. 3A illustrates the operation of the device 10 in a first case. The line A represents atrial events, for example events in the right atrium RA. The line 1V relates to events in a first ventricle 1V. The line 2V relates to events in the second ventricle 2V. As has been explained above, the first ventricle is in this case defined as the ventricle that is to be paced first if both ventricles are paced with a first time delay VV. The events shown in FIG. 3A thus occur on a time scale that is indicated by t. FIG. 3 A first illustrates that an atrial event, a P-wave, is sensed. After a certain time a pacing pulse 71 is delivered with the first pacing circuit 18. Also an evoked response 73 is shown on the line 1V. After the first time delay VV a pacing pulse 74 is delivered with the second pacing circuit 19. Also in this case an evoked response 75 is shown. Later a signal 76 is in this case sensed by the first sensing circuit 16. Since this signal is typical for an R-wave and is not preceded by any atrial event since the last ventricular events, the signal 76 is categorized as a PVC. Since the signal 76 is sensed by the first sensing circuit 16 (which relate to the ventricle that is normally paced first), a pacing pulse 77 is delivered by the second pacing circuit 19 after the second time delay $VV_{PVC1}$. As will be explained in connection with FIG. 4, the pacing pulse 77 could be inhibited in case an event is sensed by the second sensing circuit 17 during the second time delay $VV_{PVC1}$. The time delay $VV_{PVC1}$ is set to optimize the synchronization of the depolarization of the ventricles. Thereby, the likelihood of an arrhythmia caused by the PVC is reduced. FIG. 3 A also shows an evoked response 78 to the pacing pulse 77.

Figure 3B:
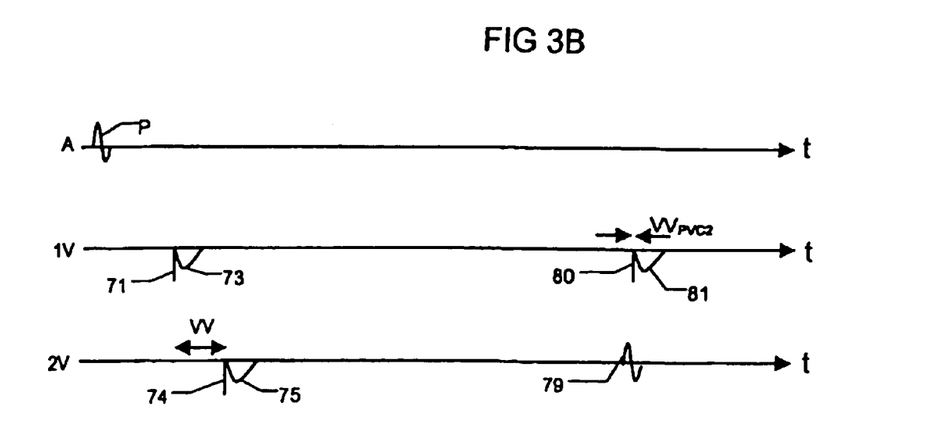
FIG. 3B schematically illustrates a similar signal sequence in a second situation of operation of the device, in accordance with the invention.

FIG. 3B shows lines corresponding to those of FIG. 3A. The events P, 71, 73, 74, 75 are the same as have been described in connection with FIG. 3A. However, in FIG. 3B, a signal 79 is sensed by the second sensing circuit 17. This signal 79 is characterized as a PVC, since no intermediate atrial event has occurred since the last ventricular events. Since the PVC 79 is in this case detected by the second sensing circuit 17, a pacing pulse 80 is delivered with a third time delay $VV_{PVC2}$ with the first pacing circuit 18 in order to reduce the risk for an arrhythmia caused by the PVC. In the shown embodiment, the third time delay $VV_{PVC2}$ is set to be substantially equal to 0. This can be beneficial if the PVC is detected by the sensing circuit that relates to the ventricle that is normally paced last if the device operates with a first time delay VV. The line 1V also shows an evoked response 81.

Figure 4:
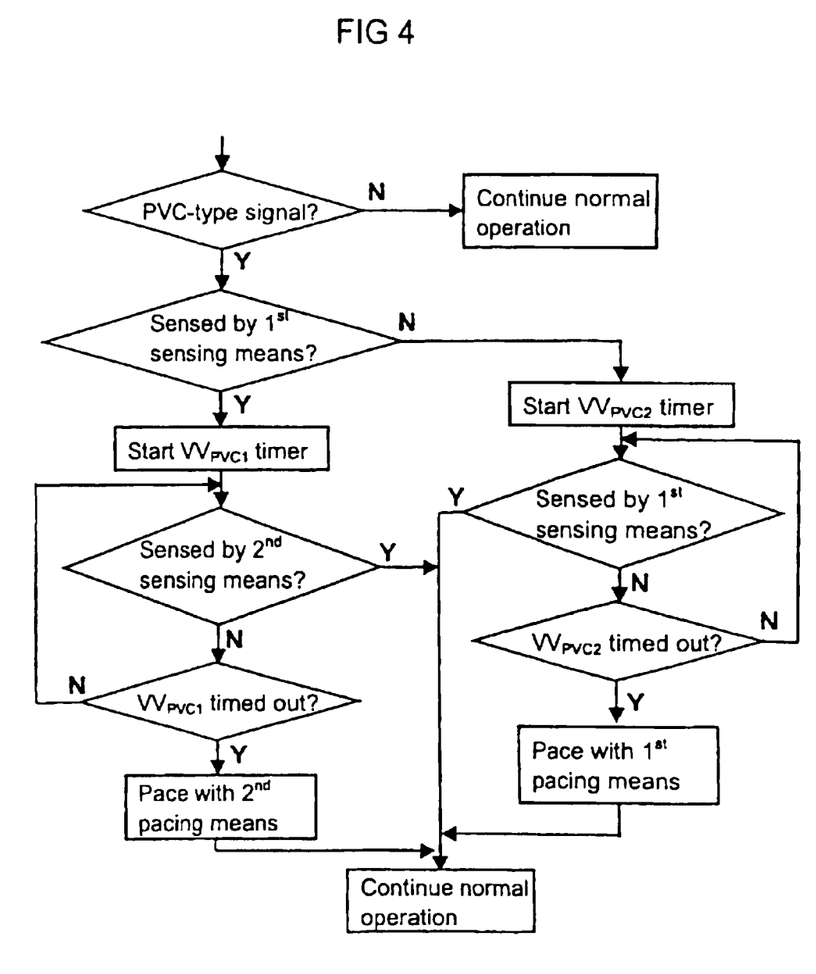
FIG. 4 is a flow chart for the operation of the device, in accordance with the invention.

FIG. 4 shows a schematic flow chart of the operation of the device 10 according to an embodiment. First it is determined whether a detected signal is to be categorized as a PVC. If this is not the case, then the normal operation of the device 10 continues. However, if the signal is typical for a PVC, then it is determined whether the signal is sensed by the first sensing circuit 16 or the second sensing circuit 17. The first sensing circuit 16 relates to the ventricle that is normally paced first. If the PVC-signal is not sensed by the first sensing circuit 16 (and therefore by the second sensing circuit 17), then a $VV_{PVC2}$-timer starts. According to an advantageous embodiment, it is thereby possible to monitor whether a signal is sensed by the first sensing circuit 16 during the $VV_{PVC2}$ time delay. If no such signal is sensed, then a pacing pulse is delivered by the first pacing circuit 18 at the time out the third time delay $VV_{PVC2}$. The device 10 then reverts back to normal operation. However, if a signal is sensed by the first sensing circuit 16 during the third time delay $VV_{PVC2}$, then no pacing signal is delivered with the first pacing circuit 18 at the timeout of the third time delay $VV_{PVC2}$. The device 10 instead reverts back to normal operation. According to one embodiment, the third time delay is set to be substantially equal to 0.

According to an alternative embodiment, it is not necessary to employ a timer for the third time delay $VV_{PVC2}$. Instead, a pacing pulse is delivered immediately with the first pacing means 18 if the PVC-signal is sensed by the second sensing circuit 17.

If the PVC-signal is sensed by the first sensing circuit 16, then a $VV_{PVC1}$-timer starts. In an embodiment, it is thereby possible to monitor whether a signal is sensed by the second sensing circuit 17 during the $VV_{PVC1}$ time delay. If no such signal is sensed, then a pacing pulse is delivered with the second pacing circuit 19 at the time out the second time delay $VV_{PVC1}$. However, if a signal is sensed by the second sensing circuit 17 during the second time delay $VV_{PVC1}$, then no pacing signal is delivered by the second pacing circuit 19 at the timeout of the second time delay $VV_{PVC1}$. The device 10 instead reverts back to normal operation.

An example of a heart stimulating system according to the invention is shown in connection with FIG. 1. The system thus includes the heart stimulating device 10 together with at least a first lead 30 and a second lead 40. A first pacing electrode 31, 32 is arranged on the first lead 30 and a second pacing electrode 41, 42 is arranged on the second lead 40. The first pacing electrode 31, 32 preferably also is used as the first sensing electrode 31, 32. Analogously, the second sensing electrode 41, 42 is the same electrode as the second pacing electrode 41, 42.

The device is preferably used according to the invention such that the system is implanted in a human or animal, wherein the first pacing electrode 31, 32 is positioned in or at a first ventricle 1V of the heart of the human or animal being and the second pacing electrode 41, 42 is positioned in or at the second ventricle 2V of the heart as exemplified in FIG. 1. The device is used, as described above, to react to a PVC in a manner such that the risk for arrhythmia is reduced. Preferably, the system is used on a human or animal suffering from congestive heart failure, for example caused by a bundle branch block.

Although modifications and changes may be suggested by those skilled in the art, it is the intention of the inventors to embody within the patent warranted hereon all changes and modifications as reasonably and properly come within the scope of their contribution to the art.

The invention claimed is:

1. An implantable heart stimulating device comprising:
   a first pacing circuit connectable to a first pacing electrode, adapted to interact with a first ventricle of a heart, to allow said first pacing circuit to deliver pacing pulses via the first pacing electrode to pace the first ventricle;
   a first sensing circuit connectable to a first sensing electrode, adapted to interact with the first ventricle, to transfer signals to the first sensing circuit to allow said first sensing circuit to sense said first ventricle;
   a second pacing circuit connectable to a second pacing electrode, adapted to interact with a second ventricle of the heart, to allow said second pacing circuit to deliver pacing pulses via said second pacing electrode to pace the second ventricle;
   a second sensing circuit connectable to a second sensing electrode, adapted to interact with the second ventricle, to transfer signals to said second sensing circuit to allow said second sensing circuit to sense said second ventricle; and
   a control circuit that operates with time cycles corresponding to normal heart cycles, said control circuit operating with a first time delay to cause, within one of said time cycles, at least said first pacing circuit to pace the first ventricle or said first sensing circuit to sense the first ventricle, and to thereafter cause said second pacing circuit to deliver a pacing pulse to the second ventricle with said first time delay, said control circuit also operating with a criterion that characterizes a signal sensed by said first sensing circuit or said second sensing circuit, that satisfies said criterion, as being in a category of signals representative of premature ventricular contraction, and said control circuit further operating with at least one of a second time delay, each different from said first time delay, and a third time delay for, within one of said time cycles, causing at least one of said first sensing circuit to sense the first ventricle and said second sensing circuit to sense the second ventricle, followed by delivery, if a predetermined pacing rule is satisfied, of a pacing pulse to the second ventricle, with said second time delay with said second pacing circuit, if the sensing was done by said first sensing circuit, or to deliver a pacing pulse to the first ventricle with said third time delay with said first pacing circuit if the sensing was done with said second sensing circuit.

2. An implantable heart stimulating device as claimed in claim 1 wherein said control circuit determines whether a signal sensed by the first or second sensing circuit is in said category and, if so, causes said first pacing circuit to deliver a pacing pulse to the first ventricle, in accordance with said predetermined pacing rule, if said signal in said category was sensed by said second sensing circuit, and to deliver a pacing pulse with said second pacing circuit to the second ventricle, in accordance with said predetermined pacing rule, if said signal in said category was sensed by said first sensing circuit.

3. An implantable heart stimulating device as claimed in claim 2 wherein said control circuit employs a rule as said predetermined pacing rule that causes said control circuit to cause said second pacing circuit to deliver the pacing pulse to the second ventricle with said second time delay, if said signal in said category is sensed by said first sensing circuit.

4. An implantable heart stimulating device as claimed in claim 3 wherein said control circuit, if said signal in said category was sensed by said first sensing circuit, thereafter monitors whether a corresponding signal is sensed by the second sensing circuit during said second time delay and, if so, said control circuit inhibits delivery of said pacing pulse with said second pacing circuit.

5. An implantable heart stimulating device as claimed in claim 2 wherein said control circuit employs a rule, as said predetermined pacing rule, that causes said control circuit to cause said first pacing circuit to deliver said pacing pulse to the first ventricle with said third time delay, if said signal in said category was sensed by said second sensing circuit.

6. An implantable heart stimulating device as claimed in claim 5 wherein said control circuit, if said signal in said category was sensed by said second sensing circuit, thereafter monitors whether a corresponding signal is sensed by the first sensing circuit during said third time delay and, if so, said control circuit inhibits delivery of said pacing pulse with said first pacing circuit.

7. An implantable heart-stimulating device as claimed in claim 1 wherein said control circuit employs delays, as each of said first, second and third time delays, that are shorter than 80 ms.

8. An implantable heart stimulating device as claimed in claim 1 wherein said control circuit employs a delay as said first time delay that is different from at least one of said second time delay and said third time delay.

9. An implantable heart stimulating device as claimed in claim 8 wherein said control circuit employs a delay, as said first time delay, that is longer than at least one of said second time delay and said third time delay.

10. An implantable heart-stimulating device as claimed in claim 1 wherein said control circuit employs a delay as said third time delay that is substantially equal to zero.

11. An implantable heart stimulating device as claimed in claim 1 further comprising a circuit arrangement adapted to interact with an atrium of the heart to sense and pace the atrium.

12. An implantable heart stimulating device as claimed in claim 11 wherein said control circuit employs a criterion, as said criterion for said category, that either a signal is sensed by the first sensing circuit after a previous sensed, paced or inhibited event relating to the first sensing circuit or the first pacing circuit, with no intervening sensed or paced event by the circuit arrangement for sensing and pacing the atrium, or that a signal is sensed by the second sensing circuit after a previous sensed, paced or inhibited event relating to said second sensing circuit or said second pacing circuit with no intervening sensed or paced event by said circuit arrangement for sensing and pacing the atrium.

13. An implantable heart stimulating system comprising:
a first pacing electrode, adapted to be positioned to interact with a first ventricle of a heart;
a first pacing circuit connected to said first pacing electrode to deliver pacing pulses via the first pacing electrode to pace the first ventricle;
a first sensing electrode, adapted to be positioned to interact with the first ventricle;
a first sensing circuit connected to said first sensing electrode to sense said first ventricle;
a second pacing electrode, adapted to be positioned to interact with a second ventricle of the heart;
a second pacing circuit connected to said second pacing electrode to deliver pacing pulses via said second pacing electrode to pace the second ventricle;
a second sensing electrode, adapted to be positioned to interact with the second ventricle;
a second sensing circuit connected to said second sensing electrode to sense said second ventricle; and
a control circuit that operates with time cycles corresponding to normal heart cycles, said control circuit operating with a first time delay to cause, within one of said time cycles, at least said first pacing circuit to pace the first ventricle or said first sensing circuit to sense the first ventricle, and to thereafter cause said second pacing circuit to deliver a pacing pulse to the second ventricle with said first time delay, said control circuit also operating with a criterion that characterizes a signal sensed by said first sensing circuit or said second sensing circuit, that satisfies said criterion, as being a category of signals representative of premature ventricular contraction, and said control circuit further operating with at least one of a second time delay, each different from said first time delay, and a third time delay for, within one of said time cycles, causing at least one of said first sensing circuit to sense the first ventricle and said second sensing circuit to sense the second ventricle, followed by delivery, if a predetermined pacing rule is satisfied, of a pacing pulse to the second ventricle, with said second time delay with said second pacing circuit, if the sensing was done by said first sensing circuit, or to deliver a pacing pulse to the first ventricle with said third time delay with said first pacing circuit if the sensing was done with said second sensing circuit.

14. An implantable heart stimulating system as claimed in claim 13 wherein said control circuit determines whether a signal sensed by the first or second sensing circuit is in said category and, if so, causes said first pacing circuit to deliver a pacing pulse to the first ventricle, in accordance with said predetermined pacing rule, if said signal in said category was sensed by said second sensing circuit, and to deliver a pacing pulse with said second pacing circuit to the second ventricle, in accordance with said predetermined pacing rule, if said signal in said category was sensed by said first sensing circuit.

15. An implantable heart stimulating device as claimed in claim 14 wherein said control circuit employs a rule as said predetermined pacing rule that causes said control circuit to cause said second pacing circuit to deliver the pacing pulse to the second ventricle with said second time delay, if said signal in said category is sensed by said first sensing circuit.

16. An implantable heart stimulating system as claimed in claim 15 wherein said control circuit, if said signal in said category was sensed by said first sensing circuit, thereafter monitors whether a corresponding signal is sensed by the second sensing circuit during said second time delay and, if so, said control circuit inhibits delivery of said pacing pulse with said second pacing circuit.

17. An implantable heart stimulating device as claimed in claim 14 wherein said control circuit employs a rule, as said predetermined pacing rule, that causes said control circuit to cause said first pacing circuit to deliver said pacing pulse to the first ventricle with said third time delay, if said signal in said category was sensed by said second sensing circuit.

18. An implantable heart stimulating system as claimed in claim 17 wherein said control circuit, if said signal in said category was sensed by said second sensing circuit, thereafter monitors whether a corresponding signal is sensed by the first sensing circuit during said third time delay and, if so, said control circuit inhibits delivery of said pacing pulse with said first pacing circuit.

19. An implantable heart stimulating system as claimed in claim 13 wherein said control circuit employs delays, as each of said first, second and third time delays, that are shorter than 80 ms.

20. An implantable heart stimulating system as claimed in claim 13 wherein said control circuit employs a delay as said first time delay that is different from at least one of said second time delay and said third time delay.

21. An implantable heart stimulating system as claimed in claim 20 wherein said control circuit employs a delay, as said first time delay, that is longer than at least one of said second time delay and said third time delay.

22. An implantable heart stimulating system as claimed in claim 13 wherein said control circuit employs a delay as said third time delay that is substantially equal to zero.

23. An implantable heart stimulating system as claimed in claim 13 further comprising a circuit arrangement adapted to interact with an atrium of the heart to sense and pace the atrium.

24. An implantable heart stimulating system as claimed in claim 23 wherein said control circuit employs a criterion, as said criterion for said category, that either a signal is sensed by the first sensing circuit after a previous sensed, paced or inhibited event relating to the first sensing circuit or the first pacing circuit, with no intervening sensed or paced event by the circuit arrangement for sensing and pacing the atrium, or that a signal is sensed by the second sensing circuit after a previous sensed, paced or inhibited event relating to said second sensing circuit or said second pacing circuit with no intervening sensed or paced event by said circuit arrangement for sensing and pacing the atrium.

25. An implantable heart stimulating system as claimed in claim 13 wherein said first sensing electrode is a same electrode as said first pacing electrode, and wherein said second sensing electrode is a same electrode as said second pacing electrode.

26. An method for stimulating a heart comprising the steps of:
implanting and positioning a first pacing electrode to interact with a first ventricle of a heart;
connecting a first pacing circuit to said first pacing electrode to deliver pacing pulses via the first pacing electrode to pace the first ventricle;
implanting and positioning a first sensing electrode to interact with the first ventricle;
connecting a first sensing circuit to said first sensing electrode to sense said first ventricle;
implanting and positioning a second pacing electrode to interact with a second ventricle of the heart;
connecting a second pacing circuit to said second pacing electrode to deliver pacing pulses via said second pacing electrode to pace the second ventricle;
implanting and positioning a second sensing electrode to interact with the second ventricle;
connecting a second sensing circuit to said second sensing electrode to sense said second ventricle; and
controlling said first and second pacing circuits and said first and second sensing circuits with a control circuit that operates with time cycles corresponding to normal heart cycles, and with said control circuit causing, within one of said time cycles, at least said first pacing circuit to pace the first ventricle or said first sensing circuit to sense the first ventricle, and to thereafter cause said second pacing circuit to deliver a pacing pulse to the second ventricle with a first time delay, employing in said control circuit a criterion that characterizes a signal sensed by said first sensing circuit or said second sensing circuit, that satisfies said criterion, as being in a category of signals representative of premature ventricular contraction, and said control circuit, within one of said time cycles, causing at least one of said first sensing circuit to sense the first ventricle and said second sensing circuit to sense the second ventricle, followed by delivery, if a predetermined pacing rule is satisfied, of a pacing pulse to the second ventricle, with a second time delay with said second pacing circuit, if the sensing was done by said first sensing circuit, or to deliver a pacing pulse to the first ventricle with a third time delay with said first pacing circuit if the sensing was done with said second sensing circuit; and
selecting said first delay to optimize hemodynamic performance of the heart and selecting at least one of said second and third delays to reduce a risk of arrhythmia of the heart.

27. A method as claimed in claim 26 comprising, in said control circuit determining whether a signal sensed by the first or second sensing circuit is in said category and, if so, causing said first pacing circuit to deliver a pacing pulse to the first ventricle, in accordance with said predetermined pacing rule, if said signal in said category was sensed by said second sensing circuit, and to deliver a pacing pulse with said second pacing circuit to the second ventricle, in accordance with said predetermined pacing rule, if said signal in said category was sensed by said first sensing circuit.

28. A method as claimed in claim 27 comprising, in said control circuit employing a rule as said predetermined pacing rule that causes said control circuit to cause said second pacing circuit to deliver the pacing pulse to the second ventricle with said second time delay, if said signal in said category is sensed by said first sensing circuit.

29. A method as claimed in claim 28 comprising in said control circuit, if said signal in said category was sensed by said first sensing circuit, thereafter monitoring whether a corresponding signal is sensed by the second sensing circuit during said second time delay and, if so, inhibiting delivery of said pacing pulse with said second pacing circuit.

30. A method as claimed in claim 27 comprising, in said control circuit employing a rule, as said predetermined pacing rule, that causes said control circuit to cause said first pacing circuit to deliver said pacing pulse to the first ventricle with said third time delay, if said signal in said category was sensed by said second sensing circuit.

31. A method as claimed in claim 30 comprising, in said control circuit, if said signal in said category was sensed by said second sensing circuit, thereafter monitoring whether a corresponding signal is sensed by the first sensing circuit during said third time delay and, if so, inhibiting delivery of said pacing pulse with said first pacing circuit.

32. A method as claimed in claim 26 comprising employing delays, as each of said first, second and third time delays, that are shorter than 80 ms.

33. A method as claimed in claim 26 comprising employing a delay as said first time delay that is different from at least one of said second time delay and said third time delay.

34. A method as claimed in claim 33 comprising employing a delay, as said first time delay, that is longer than at least one of said second time delay and said third time delay.

35. A method as claimed in claim 26 comprising employing a delay as said third time delay that is substantially equal to zero.

36. A method as claimed in claim 26 comprising implanting at least one atrial electrode in an atrium of the heart, and connecting a circuit arrangement to said atrial electrode and sensing and pacing the atrium with said circuit arrangement via said atrial electrode.

37. A method as claimed in claim 36 comprising employing a criterion, as said criterion for said category, that either a signal is sensed by the first sensing circuit after a previous sensed, paced or inhibited event relating to the first sensing circuit or the first pacing circuit, with no intervening sensed or paced event by the circuit arrangement for sensing and pacing the atrium, or that a signal is sensed by the second sensing circuit after a previous sensed, paced or inhibited event relating to said second sensing circuit or said second pacing circuit with no intervening sensed or paced event by said circuit arrangement for sensing and pacing the atrium.

38. A method as claimed in claim 26 comprising employing said at least one of said first and second time delays with values to allow reaction to said premature ventricular contraction to reduce an arrhythmia risk associated with the heart.

39. A method as claimed in claim 26 comprising implanting said first pacing electrode, said second pacing electrode, said first sensing electrode and said second sensing electrode in a living subject suffering from congestive heart failure.

40. A method as claimed in claim 26 comprising implanting said first pacing electrode, said second pacing electrode, said first sensing electrode and said second sensing electrode in a living subject suffering from a bundle branch block.

41. A method as claimed in claim 26 comprising selecting each of said first and second delays to be different from said first delay.

42. A method as claimed in claim 26 comprising selecting said first delay, said second delay and said third delay to be different from each other.

* * * * *